(12) United States Patent
Chianelli et al.

(10) Patent No.: US 8,476,060 B2
(45) Date of Patent: Jul. 2, 2013

(54) PROCESS FOR SEPARATING LIPIDS FROM A BIOMASS

(75) Inventors: Russell Chianelli, El Paso, TX (US); Calvin Hildebrand, Santa Fe, NM (US); Joaquin Rodriguez, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 315 days.

(21) Appl. No.: 12/758,480

(22) Filed: Apr. 12, 2010

(65) Prior Publication Data

US 2010/0261918 A1    Oct. 14, 2010

Related U.S. Application Data

(60) Provisional application No. 61/168,804, filed on Apr. 13, 2009.

(51) Int. Cl.
*C12N 1/06*   (2006.01)
*C12N 13/00*   (2006.01)
*C11B 1/10*   (2006.01)

(52) U.S. Cl.
USPC ............. 435/259; 435/173.1; 435/257.1; 554/8

(58) Field of Classification Search
None
See application file for complete search history.

(56) References Cited

U.S. PATENT DOCUMENTS

| | | | |
|---|---|---|---|
| 5,538,628 A | 7/1996 | Logan | |
| 5,705,722 A * | 1/1998 | Monnier et al. | 585/240 |
| 7,883,882 B2 * | 2/2011 | Franklin et al. | 435/196 |
| 2002/0001833 A1 * | 1/2002 | Ruecker et al. | 435/134 |
| 2008/0160593 A1 | 7/2008 | Oyler | |
| 2009/0000941 A1 | 1/2009 | Kropf | |
| 2009/0043118 A1 | 2/2009 | Kozyuk | |

OTHER PUBLICATIONS

Casanava, D. et al., Diesel fuel from biomass, 2007, Pure Appl. Chem., vol. 79, No. 11, pp. 2071-2081.*
Dubinsky, Z. et al., Increase of lipid yields form some algae by acid extraction, 1979, Pytochemistry, vol. 18, No. 1, pp. 51-52.*
Simon, R.D. et al., The use of an ultrasonic bath to disrupt cells suspended in volumes of less than 100 micro liters, 1974, Analytical Biochemistry, 60, pp. 51-58.*
Bioenergy Feedstock Development Program, Boifuels from Switchgrass; greener energy pastures, 2007, updated 2008, Energy Insights: special report, 19 pages (http://ww.energyinsight.net/cgi-script/csArticles/articles/000029/002996.htm).*
"Biofuels from Switchgrass: Greener Energy Pastures," http://bioenergy.ornl.gov/papers/misc/switgrs.html., 5 pages.
Dorr, T., "Biofuels for Transportation Conference," http://www.worldwatch.org/node/4094?page=0%2C7, Jun. 13, 2006, 8 pages.
Grima, E. Molina, et al., "Recovery of Microalgal Biomass and Metabolites: Process Options and Economics," Biotechnology Advances 20, (2003), pp. 491-515.

(Continued)

*Primary Examiner* — Yate K Cutliff
(74) *Attorney, Agent, or Firm* — Edwin S. Flores; Chalker Flores, LLP

(57) ABSTRACT

A novel low cost separation process for separating lipid oil from an algal biomass for biofuel production is described herein. The process of the present invention comprises of two steps: (i) breaking the algae cells and (ii) separation of the lipid oils from the broken cells. The separated lipids are extracted by conventional techniques followed by conversion to a biofuel.

11 Claims, 5 Drawing Sheets

OTHER PUBLICATIONS

Looker, D., "House Unleashes Flurry of Domestic Ethanol Support," http://www.agriculture.com/ag/story.jhtml ?storyid=/templatedata/ag/story/data/1147894145821.xml, May 17, 2006, 2 pages.

Maxwell, Eugene L., et al., "Resource Evaluation and Site Selection and Microalgae Production Systems," Solar Energy Research Institute, May 1985, 99 pages.

Saxton, Jim, "Opec and the High Price of Oil," Joint Economic Committee United States Congress, Nov. 2005, 21 pages.

Sheehan, J., et al., "A Look Back at the U.S. Department of Energy's Aquatic Species Program: Biodiesel from Algae," National Renewable Energy Laboratory, 1998, 328 pages.

* cited by examiner

PROCESS FOR SEPARATING LIPIDS FROM A BIOMASS

CROSS-REFERENCE TO RELATED APPLICATIONS

This application claims priority to U.S. Provisional Application Ser. No. 61/168,804, filed Apr. 13, 2009, the entire contents of which are incorporated herein by reference.

TECHNICAL FIELD OF THE INVENTION

The present invention relates in general to the field of biofuel production from a biomass, and more particularly, to a novel low cost separation process for separating lipid oil from an algal biomass.

STATEMENT OF FEDERALLY FUNDED RESEARCH

None.

BACKGROUND OF THE INVENTION

Without limiting the scope of the invention, its background is described in connection with a novel separation process for separating lipid oils from an algal biomass.

Approximately, two-thirds of the petroleum imported into the U.S. comes from the Middle East primarily from Saudi Arabia and Iran. This dependence on Middle Eastern oil shackles U.S foreign policy. Elimination of the U.S. dependence will involve hard work and multiple approaches. One popular approach towards energy independence is the transformation to alternate energy sources such as biodiesel[1] produced from various biomasses.

There are many biomasses that could potentially be used to produce biodiesel. However, biodiesel production from microalgal lipids has proven to be very promising. Production of oil from microalgae has been described in US Patent Application No. 20080160593 (Oyler, 2008).[2] The application describes a process for production of biofuels from algae that includes cultivating an oil-producing algae by promoting sequential photoautotrophic and heterotrophic growth. The method can further include producing oil by heterotrophic growth of algae wherein the heterotrophic algae growth is achieved by introducing a sugar feed to the oil-producing algae. The algal oil can be extracted from the oil-producing algae, and can be converted to form biofuel.

US Patent Application No. 20090043118 (Kozyuk, 2009)[3] describes a method comprising applying a controlled flow cavitation apparatus to a biodiesel production process in order to increase fatty acid alkyl ester yield. A feedstock comprising free fatty acids can be passed through a controlled flow cavitation apparatus at a velocity capable of generating a hydrodynamic cavitation zone where the free fatty acids can be esterified. One or more controlled flow cavitation apparatuses can be applied at various points of a biodiesel production process.

US Patent Application No. 20090000941 (Kropf, 2009)[4] describes an invention relating generally to chemical reactions and processes, and in particular to a method for enhancing the rate of a chemical reaction and to apparatus for carrying out the method. The invention more particularly relates to methods and apparatus which utilize microwave and ultrasonic energy to enhance chemical reaction rates; and in specific instances, the invention relates to methods, processes and apparatus for the synthesis of biodiesel fuels. The methods, processes and apparatus of the invention are useful for the synthesis of biodiesel fuels; and also useful for production of reaction products of esterification and/or transesterification reactions including fatty acid alkyl esters.

SUMMARY OF THE INVENTION

The separation of lipid oil from algae is a major issue in developing biofuels from algae. The present invention describes a two stage process to (i) breaking of the algae cells and (ii) separation of the lipid oils from the broken cells. In the first step, a sonic device known as a SOLOTON is used to break the algae cells creating a completely dispersed emulsion "pea soup" of broken algae cells, lipids, and growth media. In the second step, a novel chemical treatment with acid released the lipid oil from the "pea soup" and at least two phases (lipid oil/water dispersed broken cells) are created. The oil may then be extracted with conventional techniques.

In one embodiment, the present invention describes a process for lysing one or more microalgal cells, wherein the lysis results in the extraction of one or more algal lipids. The process comprises the steps of: (i) cultivating a hydrocarbon or a lipid-producing microalgae in a growth media, wherein the cultivation is carried out under one or more growth conditions comprising sunlight, nutrients, water, and $CO_2$, (ii) exposing the microalgae to low energy soundwaves in a sonicating device (e.g., using a sonic device) to produce a homogenous algal slurry comprising broken algal cells, algal lipids and the growth media, wherein the homogeneous algal slurry comprises a lipid/oil top layer, a green layer comprising lysed microalgal cells and a clear water layer, (iii) extracting one or more algal lipids from the algal slurry by a chemical treatment, wherein the chemical treatment may include, but is not limited to the addition of heat, acid, and chemicals to break an oil/water emulsion, (iv) exposing the homogeneous algal slurry to low energy soundwaves in the sonicating device to break the oil/water emulsion, wherein the exposure of the homogeneous algal slurry to low energy soundwaves is an optional treatment step, and (v) extracting of the one or more algal lipids.

In one aspect the process further comprises the step of converting the extracted one or more algal lipids to a renewable fuel or a biofuel. In another aspect of the present invention the sonicating device is a SOLOTON device. In further aspects the low energy soundwaves have a maximum frequency of 2 MHz and the flow rate of the microalgal cells suspended in the growth media into the SOLOTON is varied. In yet another aspect the acids used to extract the one or more algal lipids from the algal slurry are selected from at least one of nitric acid, sulfuric acid, hydrochloric acid, phosphoric acid, acetic acid, inorganic acids or organic acids used in concentrations of 0.01M, 0.05M, 0.1M, 0.25M, 0.5M, 0.75M, and 1.0M In a further aspect the lipid-producing algae includes an algae selected from the group consisting of diatoms (bacillariophytes), green algae (chlorophytes), blue-green algae (cyanophytes), golden-brown algae (chrysophytes), haptophytes, and combinations thereof. In a specific aspect the lipid-producing algae is selected from one or more of *Amphipleura, Amphora, Chaetoceros, Chlorella, Cyclotella, Cymbella, Fragilaria, Hantzschia, Navicula, Nitzschia, Phaeodactylum, Thalassiosira, Ankistrodesmus, Botryococcus, Chlorella, Chlorococcum, Dunaliella, Monoraphidium, Oocystis, Scenedesmus, Tetraselmis, Oscillatoria, Synechoccus, Boekelovia*, or combinations thereof.

In one aspect the present invention describes a step of converting algal oil into the renewable fuel or the biofuel by direct hydrogenation of the algal oil to produce the biofuel. In a related aspect the step of converting algal oil into biofuel comprises the conversion of lipid to biofuel by transesterfication of the algal oil to produce the biofuel.

One aspect of the present invention is directed towards forming a lipid product formed by the process described in the embodiment of the present invention. In related aspects the lipid product is substantially free of sulfur, comprises a fatty acid ethyl ester, and an alkane.

In another embodiment the present invention describes a system for production of a renewable fuel or a biofuel from one or more microalgae, comprising: one or more microalgal growth reservoirs, one or more microalgal homogenizers connected to the reservoirs, the homogenizers comprising an apparatus that creates a homogenous slurry comprising broken microalgal cells, growth media, and algal lipids by breaking the microalgal cells using low energy soundwaves to produce the homogeneous algal slurry, one or more algal lipid extraction vessels connected to the homogenizers, wherein the algal lipids are extracted by a chemical treatment; wherein the chemical treatment may include, but is not limited to the addition of heat, acid, and chemicals to break an oil/water emulsion and one or more converters connected to the extracted algal lipid vessel, wherein the algal lipids are converted into the renewable fuel or the biofuel.

In a related aspect the one or more converters are configured for conversion by direct hydrogenation of the algal oil to produce the renewable fuel or the biofuel. In another aspect the one or more converters are configured for conversion by transesterfication of the algal oil to produce the renewable fuel or the biofuel. In yet another aspect the algae are grown under conditions that stimulate accumulation of lipids selected from at least one of light stimulation, nutrient stimulation, injection of a reactive carbon dioxide source, and nutrients. The microalgae used in the system of the instant invention include an algae selected from the group consisting of diatoms (bacillariophytes), green algae (chlorophytes), blue-green algae (cyanophytes), golden-brown algae (chrysophytes), haptophytes, and combinations thereof.

BRIEF DESCRIPTION OF THE DRAWINGS

For a more complete understanding of the features and advantages of the present invention, reference is now made to the detailed description of the invention along with the accompanying figures and in which:

(FIG. 5A) in the sample treated by the SOLOTON the "pea soup" separated in to three layers; (i) lipid/oil on the top, (ii) a very thin green layer, and (iii) the water layer and (FIG. 5B) in the untreated layer no separation is observed. The thin green layer between the lipid/oil layer and the water layer consists of disrupted algal cell walls.

DETAILED DESCRIPTION OF THE INVENTION

Figure 1:
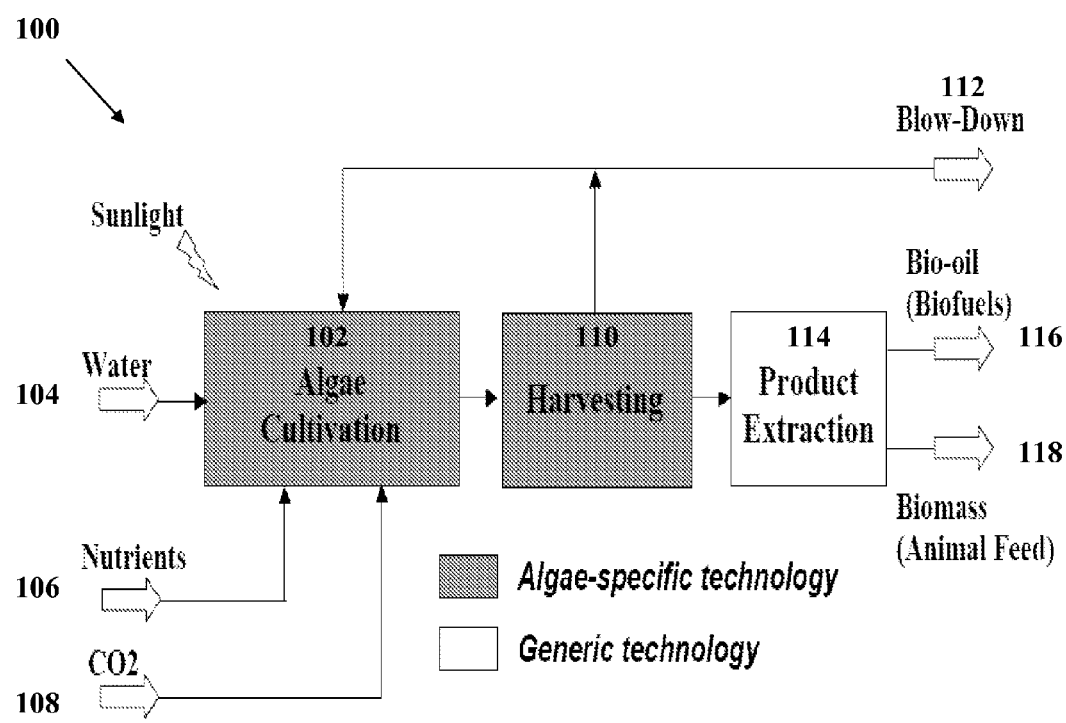
FIG. 1 is a schematic showing the process of biofuel production in algae.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "algae" represents a large, heterogeneous group of primitive photosynthetic organisms which occur throughout all types of aquatic habitats and moist terrestial environments. Nadakavukaren et al., Botany. *An Introduction to Plant Biology*, 324-325, (1985). The term "algae" as described herein is intended to include the species selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*. The term "homogenizer" is used in the general sense of a grinder, and often no pressure limitations or initial, i.e. prehomogenization, particle size required in order to achieve the desired particle size are specified.

The term "microalgae" as used herein includes all forms of microscopic aquatic plants including mixtures of Green and Bluegreen Algae, preferably uni-cellular non-filamentous noncolonial types, to which photosynthetic bacteria may also be added. The term "microalgae" also refers to algae that are smaller than approximately 2 centimeters in height or length.

The term "interface" as used herein indicates a boundary between any two immiscible phases. The term "lysing" refers to the action of rupturing the cell wall and/or cell membrane of a cell. The term "lysing" does not require that the cells be completely ruptured, rather, "lysing" can also refer to the release of intracellular material.

As used herein the term "esterification" or "transesterification" are the processes by which an acid group is added, hydrolyzed, repositioned or replaced on one or more components of the substrate. The acid group can be derived from a fat or oil which is part of the initial substrate, or from a free fatty acid or ester that has been added to the deodorized substrate or purification media-processed substrate. The term "transesterification" includes the process in which R, R' or R" on a glyceride is a first fatty acid group given by —OC(=O)R''', and the first fatty acid group is replaced by a second, different fatty acid group. The second fatty acid group which replaces the first fatty acid group can come from the same or different fat or oil present in the initial substrate. The second fatty acid can also come from a free fatty acid or ester added to the deodorized substrate or the purification media-processed substrate.

The term "biodiesel" used in this specification includes mono alkyl esters of a long chain fatty acid derived from renewable lipid sources. Suitable sources include animal fats and vegetable oils, including, for example, soybean oil, sunflower oil, linseed oil, coconut oil, and the like. Other useful biodiesel materials for use in the present invention comprise a mixture of fatty acid esters. Typically these materials are made by the transesterification of vegetable oil to biodiesel. One route to biodiesel involves reacting a vegetable oil (a triglyceride) with an alcohol, preferably methanol, to form biodiesel and glycerol. Biodiesels can comprise methyl esters that contain, for example, $C_6$-$C_{14}$ fatty acids such as caproic, caprylic, capric, lauric, and myristic. The term "biodiesel " can also include, for example, methyl esters of $C_{12}$-$C_{22}$ fatty acids such as lauric acid, myristic acid, palmitic acid, palmitoleic acid, stearid acid, oleic acid, elaidic acid, petroselic acid, ricinoleic acid, elaeosteric acid, linoleic acid, linolenic acid, arachic acid, gadoleic acid, behenic acid and erucic acid. It should be understood however, that, in other embodiments, other useful biodiesel materials and mixtures of these and other biodiesels, are within the contemplated scope of the present invention.

As used herein, the term "biofuel" or "biomass" refers to organic matter harvested or collected as a source of energy. Specifically, biofuel refers to a source material that is derived from non-fossilized organic matter and available on a renewable or recurring basis, as compared with a fossil fuel, which is derived from fossilized organic matter and is not considered to be "renewable." Biofuels are typically obtained from production waste streams, i.e., production byproducts, although they can also be obtained from sources specifically designed to produce biofuels. There are generally considered to be three types of biofuels, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels also encompass either a 100% biodiesel or a mixture comprising biodiesel and regular petroleum-based diesel from a refinery The instant invention describes a two stage process herein below for breaking or lysing one or more algae cells and for the separation of the lipid oils from the broken cells. In a first step, a sonic device known as a SOLOTON is used to break the algae cells creating a completely dispersed emulsion "pea soup" of broken algae cells, lipids, and growth media. This is followed by a novel chemical treatment step wherein the acid released the lipid oil from the "pea soup" and at least two phases (lipid oil/water dispersed broken cells) are created. The oil can then be extracted with conventional techniques.

The need for new liquid fuel sources is evident everyday in the news and at the gas pump. Entire industries including airlines and trucking are at risk because of rapidly rising fuel prices and undependable oil exporters in the Middle East and Africa. In Feb. of 2006, President Bush stated that the United States of America must break its dependence on petroleum ("America is addicted to oil").[1] Approximately two-thirds of the petroleum imported into the U.S. comes from the Middle East primarily from Saudi Arabia and Iran. This dependence on Middle Eastern oil shackles U.S foreign policy. Elimination of the U.S. dependence will involve hard work and multiple approaches. Solving this problem requires new technologies to produce substitutes for gasoline, diesel, and jet fuel. The Chairman of the Advisory Board of the Clean Fuels Foundation believes that this transformation should be coupled with a transformation to alternate energy sources such as biodiesel.[5]

The current political climate in the U.S. is urging a shift to independence from foreign oil sources and an overall understanding for the need to seek out new energy sources is becoming more prevalent among the general public. The shift to alternative fuels is exemplified by The Energy Development for a Growing Economy (EDGE) bill introduced in the senate in May 2006 which calls for 25% of vehicles sold in the U.S. to run on an alternative fuel by the year 2010.[6] Because, biodiesel can be used with little or no modifications required on diesel engines, minor manufacturing technology and infrastructure modifications to the petroleum economy are needed for biofuels to gain significant market share.[7] The transformation to alternate energy sources such as biodiesel will result in a significant decrease in $CO_2$ greenhouse gas emission. Thus, the introduction of biodiesel will help accomplish the dual goal of energy security and improvement of the environment.

Over the next 20 years, energy consumption in the U.S. is projected to rise by 30%; yet domestic energy production is only expected to grow by 25%. Petroleum imports already supply more than 55% of U.S. domestic needs, and they are expected to grow to more than 68% by 2025 as worldwide oil demand continues to rise and domestic oil production continues to decline. This increased reliance on imported sources of energy threatens national security, the economy and future competitiveness. The alternative energy industry is therefore poised for growth. Biodiesel offers many advantages over traditional petroleum diesel in that it is made from renewable resources (biomass), is biodegradable, nontoxic and contains no sulfur. Although relatively new, growth in the U.S. biodiesel industry has gone from 2 million gallons in 2000, 25 million gallons in 2004, 91 million gallons in 2005[5] and these increases are expected to accelerate.

Because, biodiesel can be used with little or no modifications required on diesel engines, only minor manufacturing technology and infrastructure modifications are needed for this particular biofuel to gain significant market share.[5] Biodiesel offers many advantages over traditional petroleum diesel in that it is made from renewable resources (biomass), is biodegradable, is nontoxic, and contains no sulfur. Although relatively new, US biodiesel production has gone from 2 million gallons in 2000, 25 million gallons in 2004, to 91 million gallons in 2005[8] and is growing at an exponential rate.

A variety of biomass sources are presently being used to produce biodiesel including soybeans, rapeseed, jatropha, and palm oil. There are many biomasses that could potentially be used to produce biodiesel. However, biodiesel production from micro-algal lipids has proven to be very promising. In 1998, the National Renewable Energy Laboratory completed a review of the Aquatic Species Program (ASP 1976-1996) to develop renewable transportation fuels from algae.[9] The program catalogued progress in the biology; biochemistry and engineering of lipid producing algae grown in open ponds. However, at the writing of the report the price of oil was fluctuating between $20 and $25 per barrel of oil.[10] Thus, the economic viability of biodiesel from algae was marginal in 1998. This situation is significantly different at the current $100-150 per barrel.

Present efforts to commercialize microalgae for biodiesel production are based on 20 years of federally funded work under the Aquatic Species Program (ASP 1976-1996). The data in Table 1 compares the number of US gallons that may be produced annually per acre by different "bio-fuel" crops. Microalgae can produce from 7 to 400 times more fuel per acre than any terrestrial plant because they are more efficient lipid producers and grow more rapidly. Many of the species of microalgae collected during the Aquatic Species Program (ASP) produced up to 60% of their body weight in the form of lipids that could then be converted into biodiesel.

TABLE 1

Estimated Liquid Fuel Production Per Acre Per Year for Various Biomass Crops.[11-13]

| ENERGY CROP | FUEL PRODUCTION (US Gals/acre/year) |
|---|---|
| Soybean | 40-50 |
| Rapeseed | 110-145 |
| Mustard | 140 |
| Jatropha | 175 |
| Switchgrass | 1500 |
| Palm Oil | 650 |
| Algae | 10,000-20,000 |
| Sugar Cane | 662 |
| Sugar Beet | 714 |

The scalable impact of commercial biodiesel production from microalgae is exemplified by the fact that cultivation of microalgae over a surface of 38,500 km$^2$ in a zone of high sun-exposure such as the Sonora Desert would make it possible to replace all US petroleum consumption.

A report investigating available underutilized saline water supplies, large areas of underutilized land and climatic conditions identified the US Southwest as ideally suited for the farming of microalgae for biofuel production from algal lipids.[14] Furthermore, the use of brackish water and low-valued land would not compete with agriculture or cities for freshwater and desirable land.

The work performed under the Aquatic Species Program identified algae species best suited for biodiesel production; little research was conducted on downstream processes such as the large-scale (economical) harvesting of algae, extraction of lipids from algae, and commercial-scale production of high value products like lubricants, healthcare products, and biodiesel from microalgal oils and lipids. Separation of the algae and extraction of the lipid from the algae represent 30% or more of the cost of producing biofuel.[5]

FIG. 1 is a schematic representation 100 detailing the production of a biofuel from an algal biomass. In the first step the biofuel producing algae are cultivated in a growth reservoir 102 under favorable growth conditions (water, sunlight, $CO_2$, and nutrients), supplied through inlets 104, 106, and 108 to the reservoir 102. The algal biomass is harvested after a specified number of days and transferred to vessel 110. The algal biomass is separated and dried 112. This is followed by extraction of the product (oils and lipids) by traditional solid-liquid extraction techniques in an extraction vessel 114. The extracted product is further subjected to chemical processes for conversion to a biofuel 116. The biomass left over after the extraction of the oils and lipids is used as animal feed 118.

The present invention discloses a novel process for separation of lipids from algal biomass that has low energy input, is rapid, and uses low cost chemical reagents using a patented device known as a SOLOTON. The detailed description of which is found in U.S. Pat. No. 5,538,628 (Logan, 1996), relevant portions incorporated herein by reference.[16] The unit pictured will process 2,000 BBL/day of liquid. The unit runs on standard 120 volt electric service and is driven by a normal stereo amplifier with a specialized waveform input to produce sound waves. Because the SOLOTON operates on 120 volts, the energy input is very low in contrast with other sonochemical processes in which the energy input is prohibitive. The algal slurry passes through the SOLOTON rapidly and produces homogenous algal slurry now composed of broken algal cells and released algal lipids. The SOLOTON affects this emulsification process as opposed to breaking chemical bonds.

Figure 2:
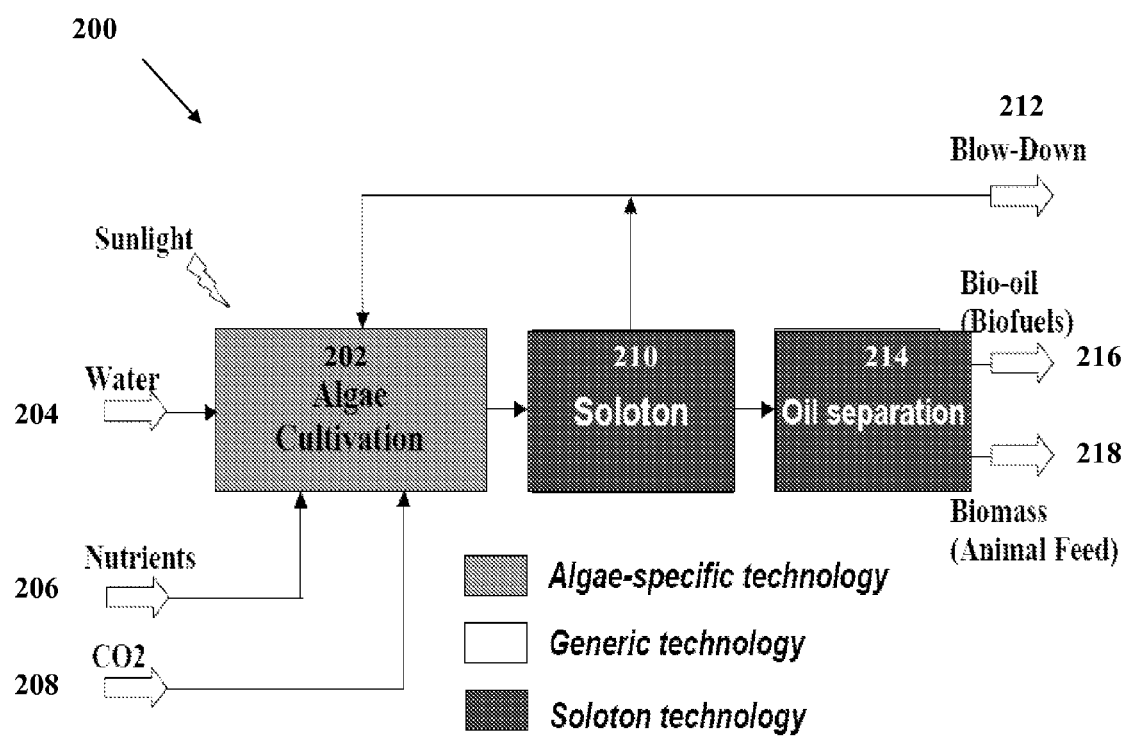
FIG. 2 is a schematic of the present invention showing the use of the SOLOTON sonic device for biofuel production in algae.

FIG. 2 is a schematic representation of the method 200 of the present invention, showing the use of the SOLOTON device 210 in the production of a biofuel from an algal biomass. The biofuel producing algae are cultivated in a growth reservoir 202 in the presence of sunlight. Additional nutrients, water, and $CO_2$, are supplied to the reservoir 202 through the inlets 204, 206, and 208. After allowing a specified amount of time for growth in the reservoir 202, the algal biomass is passed through the SOLOTON device 210 for processing. The processed sample forms a "pea soup" 214 comprising of three layers: lipid/oil on top, a very thin green layer, and then the water layer. The lipid/oil top layer is separated using traditional separation techniques (acid extraction, etc) and the extracted oil is subjected to further processing to produce the biofuel 216. The biomass left over after the extraction of the oils and lipids is used as animal feed 218

Figure 3:
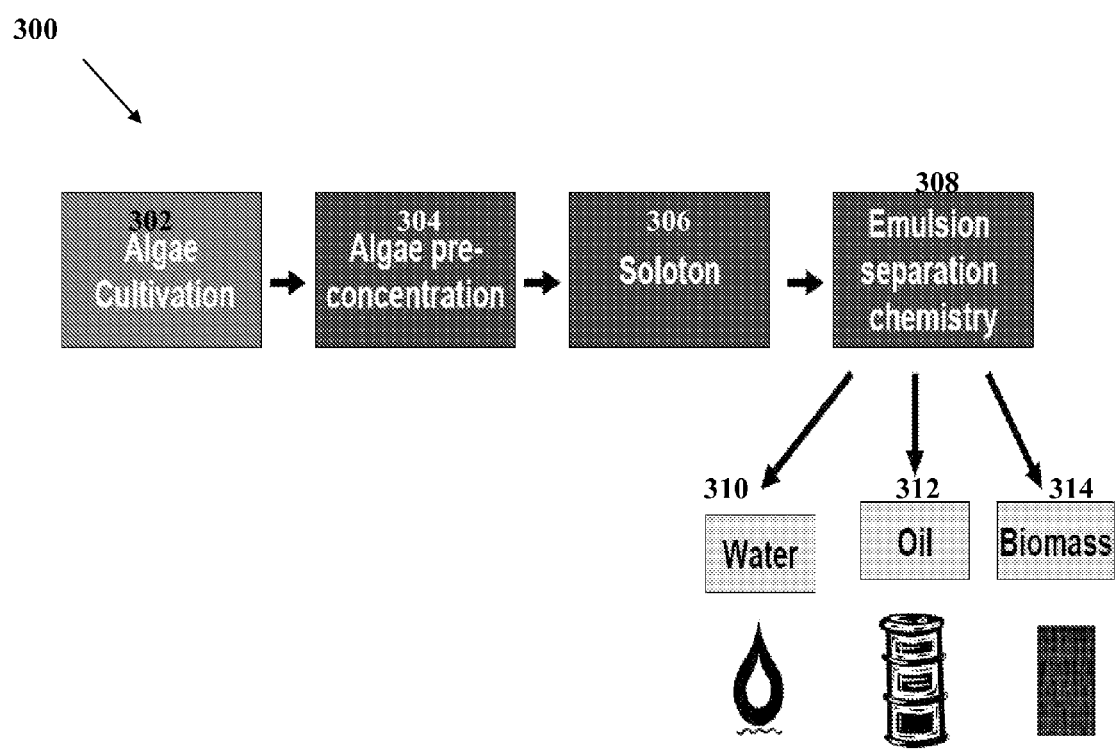
FIG. 3 shows the use of the SOLOTON sonic device as envisioned by the present invention.

FIG. 3 is a schematic representation 300 of the end products after SOLOTON device processing 306 and emulsion separation chemistry 308. The sample 304 after the SOLTON 306 has three distinct layers a lipid/oil layer 312, a layer containing the algal biomass 314, and a water layer 310. The SOLOTON process 306 as detailed by the present invention obviates the step of drying and conventional separation of the algal biomass 314 from the product.

Figure 4:
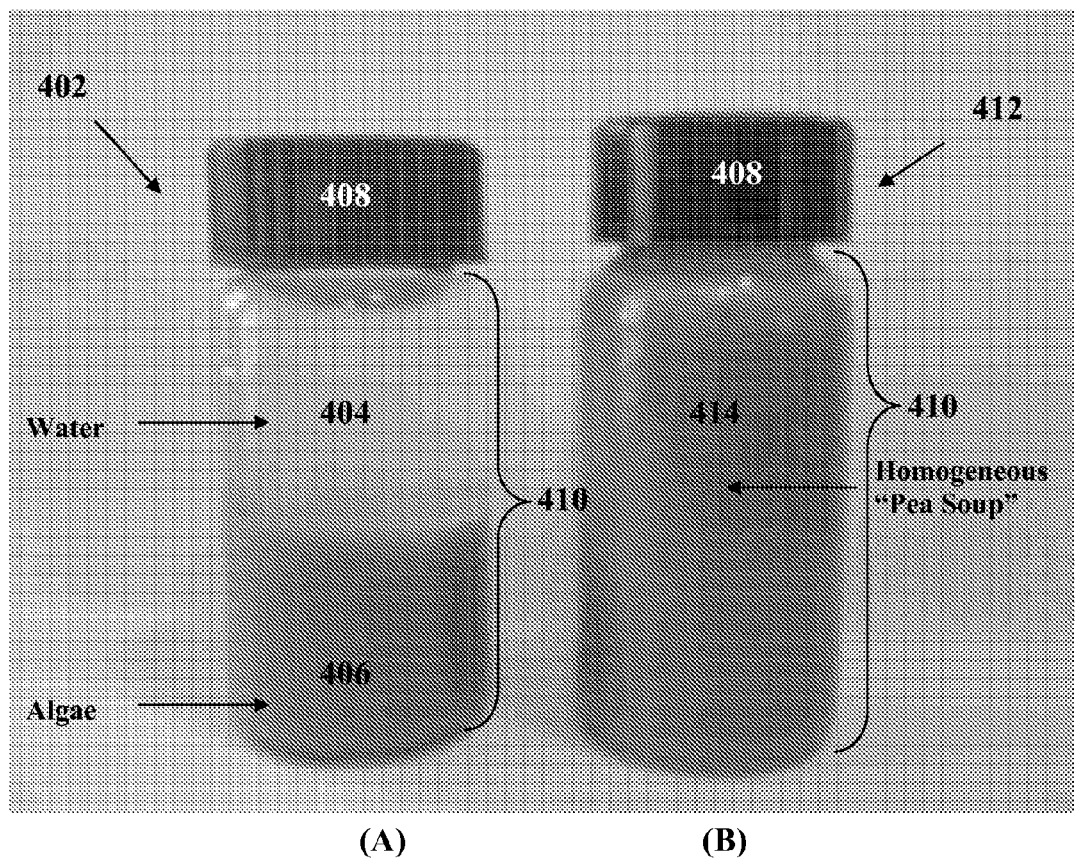
FIG. 4 represents the algal biomass before and after the treatment in the SOLOTON sonic device: (A) before treatment in the SOLOTON the algal biomass solution has two phases (water on top and algae at the bottom), and (B) after the SOLOTON the solution is homogenous and has the consistency of "pea soup"

FIG. 4 represents the algal biomass before 402 and after 412 the treatment in the SOLOTON sonic device: (a) before treatment in the SOLOTON the algal biomass solution has two phases (water on top 404 and algae 406 at the bottom), and (b) after the SOLOTON the solution is homogenous and has the consistency of "pea soup" 414.

Figure 5A:
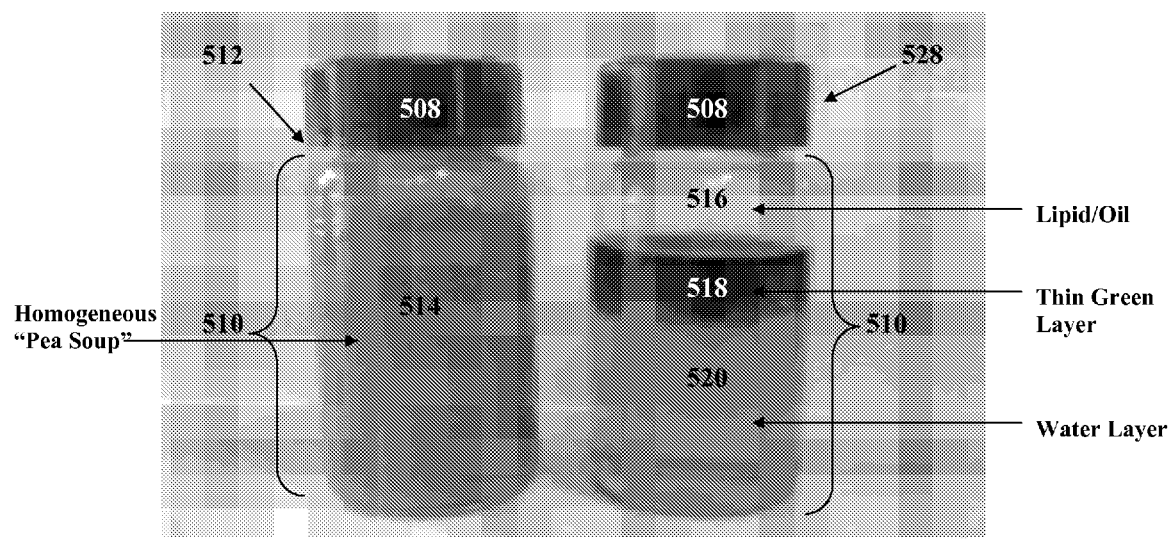
FIGS. 5A and 5B shows the effect of a simple chemical treatment on the treated and untreated samples shown in FIG. 4.
Figure 5B:
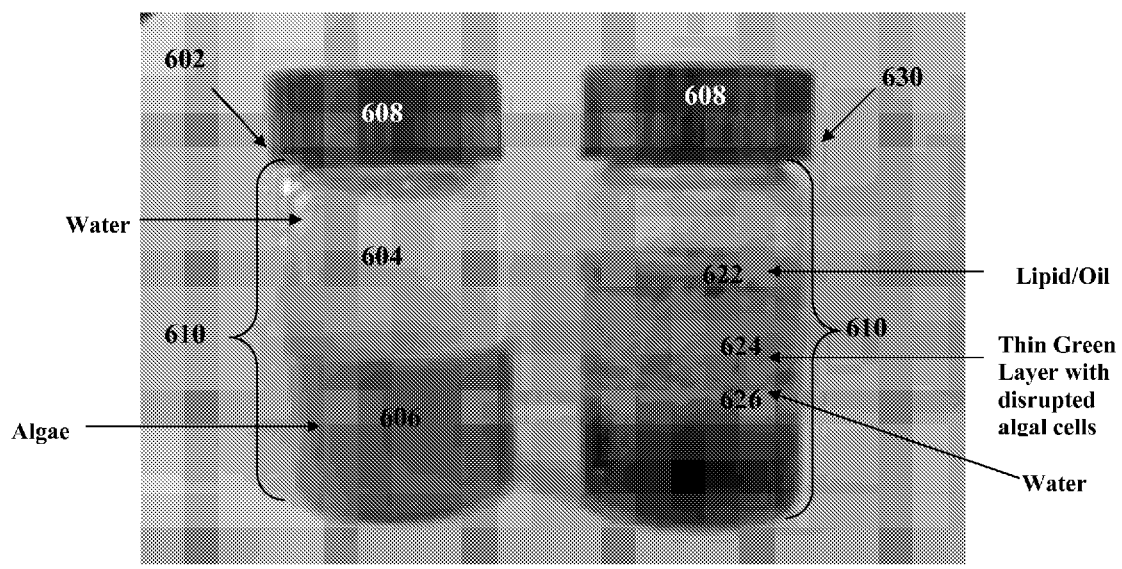

FIGS. 5A and 5B shows the effect of a simple chemical treatment 528 and 630 on the treated 512 and untreated 602 samples shown in FIG. 4, respectively. In the sample 512 treated by the SOLOTON, the "pea soup" 514 separated into three layers: lipid/oil on top 516, a very thin green layer 518, and then the water layer 520. The thin green layer 518 between the lipid/oil layer 516 and the water layer 520 consists of disrupted algal cell walls. In the untreated samples 602 no separation is observed.

Due to the simplicity, rapidness and low cost of this process, the present invention represents a significant advance over existing techniques for separating and recovering algal lipids.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] MSNBC News Services Feb. 1, 2006
[2] US Patent Application No. 20080160593.
[3] US Patent Application No. 20090043118.
[4] US Patent Application No. 20090000941.
[5] R. James Woolsey personal communication Jul. 2006.
[6] D. Looker, Congress unleashes flurry of domestic ethanol support, http://www.agriculture.com/ag/story.jhtml?storyid=/templatedata/ag/story/data/1147894145821.xml, May 17, 2006
[7] A. Karsner, Hydrogen Economy, http://www.eere.energy.gov/news/speeches/2006-05-16_hydrogen.cfm, May 16, 2006.
[8] T. Dorr, Biofuels for Transportation Conference, http://www.worldwatch.org/node/4094?page=0%2C7, Jun. 13, 2006.
[9] J. Sheehan, T. Dunahay, J. R. Benemann, and P. Roessler, A Look Back at the U.S. Department of Energy's Aquatic Species Program-Biodiesel from Algae" National Renewable Energy Laboratory, 1998.
[10] *OPEC and the High Price of Oil*, Joint Economic Committee United States Congress, Chairman Jim Saxton, 2005.
[11] http://www.unh.edu/p2/biodiesel/article_algae.html.
[12] http://www.globalfootprints.org/isues/local/transport/biofuels.htm.
[13] http://bioenergy.ornl.gov/papers/misc/switgrs.html.
[14] E. L. Maxwell, A. G. Folger, S. E. Hogg. 1985. Resource evaluation and site selection for microalgae production systems. Solar Energy Research Institute, Golden.
[15] M. E. Grima, E. H. Belarbi, F. G. Acien Fernandez, and A. Robles Medina. Recovery of microalgal biomass and metabolites: process options and economics. *Biotechnology Advances*. 20 (2003): 491-515.
[16] U.S. Pat. No. 5,538,628.

What is claimed is:

1. A process for lysing one or more microalgal cells, wherein the lysis results in an extraction of one or more algal lipids, comprising the steps of:
cultivating a hydrocarbon or a lipid-producing microalgae in a growth media, wherein the cultivation is carried out under one or more growth conditions comprising sunlight, nutrients, water, and CO2;
exposing the microalgae to low energy soundwaves in a sonicating device to produce a homogenous algal slurry comprising broken algal cells, algal lipids, and the growth media, wherein the homogeneous algal slurry comprises a lipid/oil top layer, a green layer comprising lysed microalgal cells, and a clear water layer;
extracting one or more algal lipids from the homogenous algal slurry by a chemical treatment, wherein the chemical treatment may include, but is not limited to the addition of heat, acid, and chemicals to break an oil/water emulsion;
exposing the homogeneous algal slurry to low energy soundwaves in the sonicating device to break the oil/water emulsion, wherein the exposure of the homogeneous algal slurry to low energy soundwaves is an optional treatment step; and
extracting of the one or more algal lipids.

2. The process of claim 1, further comprising the step of converting the extracted one or more algal lipids to a renewable fuel or a biofuel.

3. The process of claim 2, wherein the step of converting the extracted one or more algal lipids into the renewable fuel or the biofuel comprises the conversion of algal lipids to the biofuel by direct hydrogenation of the algal lipids to produce the biofuel.

4. The process of claim 2, wherein the step of converting the extracted one or more algal lipids into biofuel comprises the conversion of algal lipids to biofuel by transesterfication of the algal lipids to produce the biofuel.

5. The process of claim 1, wherein the sonicating device is a SOLOTON device.

6. The process of claim 1, wherein the low energy soundwaves have a maximum frequency of 2 MHz.

7. The process of claim 1, wherein a flow rate of the microalgae suspended in the growth media into the sonicating device is varied.

8. The process of claim 1, wherein the acids used to extract the one or more algal lipids from the algal slurry are selected from at least one of inorganic acids or organic acids.

9. The process of claim 1, wherein the acids used to extract the one or more algal lipids are used in concentrations of 0.01M, 0.05M, 0.1M, 0.25M, 0.5M, 0.75M, and 1.0M.

10. The process of claim 1, wherein the lipid-producing microalgae includes an algae selected from the group consisting of diatoms (bacillariophytes), green algae (chlorophytes), blue-green algae (cyanophytes), golden-brown algae (chrysophytes), haptophytes, and combinations thereof.

11. The process of claim 1, wherein the lipid-producing microalgae is selected from one or more of *Amphipleura, Amphora, Chaetoceros, Chlorella, Cyclotella, Cymbella, Fragilaria, Hantzschia, Navicula, Nitzschia, Phaeodactylum, Thalassiosira, Ankistrodesmus, Botryococcus, Chlorella, Chlorococcum, Dunaliella, Monoraphidium, Oocystis, Scenedesmus, Tetraselmis, Oscillatoria, Synechococcus, Boekelovia*, or combinations thereof.

\* \* \* \* \*